United States Patent
Yamada et al.

(10) Patent No.: US 9,632,023 B2
(45) Date of Patent: Apr. 25, 2017

(54) V-BLOCK REFRACTOMETER

(71) Applicant: SHIMADZU CORPORATION, Kyoto-shi, Kyoto (JP)

(72) Inventors: Katsuto Yamada, Kyoto (JP); Naoya Kondo, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 14/901,762

(22) PCT Filed: Jul. 4, 2013

(86) PCT No.: PCT/JP2013/068410
§ 371 (c)(1),
(2) Date: Dec. 29, 2015

(87) PCT Pub. No.: WO2015/001649
PCT Pub. Date: Jan. 8, 2015

(65) Prior Publication Data
US 2016/0238525 A1 Aug. 18, 2016

(51) Int. Cl.
*G01N 21/41* (2006.01)

(52) U.S. Cl.
CPC ...... *G01N 21/4133* (2013.01); *G01N 2201/061* (2013.01); *G01N 2201/068* (2013.01); *G01N 2201/0633* (2013.01)

(58) Field of Classification Search
CPC ......... G01N 21/4133; G01N 2201/061; G01N 2201/0633; G01N 2201/068; G01N 21/41
USPC ................................................ 356/300–334
See application file for complete search history.

(56) References Cited

U.S. PATENT DOCUMENTS

2013/0182245 A1* 7/2013 Yasunaga ............... G01N 21/41
356/135

* cited by examiner

*Primary Examiner* — Tri T Ton
(74) *Attorney, Agent, or Firm* — Sughrue Mion, PLLC

(57) ABSTRACT

A V-block refractometer capable of enhancing measurement accuracy is provided. An incident angle of measurement light incident on a V-block prism 1 from a collimator lens 48 is changed through the rotation of a motor 7, and the measurement light from the V-block prism 1 at each incident angle is detected by a detector 2. This configuration eliminates the need to provide the detector 2 near the motor 7 as in the conventional art, whereby deterioration in measurement accuracy caused by an increase in load to the motor 7 can be prevented, and the measurement accuracy can be enhanced.

4 Claims, 5 Drawing Sheets

V-BLOCK REFRACTOMETER

CROSS REFERENCE TO RELATED APPLICATIONS

This is a National Stage of International Application No. PCT/JP2013/068410 filed Jul. 4, 2013, the contents of which are incorporated herein by reference in its entirety.

TECHNICAL FIELD

The present invention relates to a V-block refractometer that measures a refractive index of a sample by irradiating the sample with measurement light through a V-block prism.

BACKGROUND ART

In a V-block refractometer, a sample is placed on a V-shaped groove formed on a V-block prism, and the sample is irradiated with measurement light through the V-block prism. The measurement light passing through the sample is detected by a detector, whereby a refractive index of the sample can be measured (see Patent Document 1 below, for example).

FIG. 5 is a schematic plan view illustrating an example of a configuration of a conventional V-block refractometer. The refractometer includes, in addition to the above V-block prism 101 and the detector 102, a light source unit 103 that emits measurement light, a first optical system 104 that guides the measurement light from the light source unit 103 to the V-block prism 101, and a second optical system 105 that guides the measurement light passing through the V-block prism 101 to the detector 102.

The light source unit 103 includes a mirror 132 that is rotatable about a rotation shaft 131 extending in the perpendicular direction (front-to-back direction of the sheet of FIG. 5), and a plurality of light sources 133 that is arranged in an arc about the rotation shaft 131 and capable of emitting measurement light having different wavelengths. With this, the measurement light from the light source 133 according to the rotation position of the mirror 132 can be reflected on the mirror 132 in the horizontal direction, and guided toward the first optical system 104.

The first optical system 104 includes a lens 141, mirrors 142, 143, and 144, an interference filter 145, a slit 146, a collimator lens 147, and the like. Measurement light passing through the lens 141 and reflected on the mirrors 142 and 143 is incident on the interference filter 145 selected according to the type of the light sources 133, and only the measurement light (monochromatic light) having a specific wavelength passes through the interference filter 145. The measurement light passing through the interference filter 145 is reflected on the mirror 144, passes through the slit 146, is converted into parallel light by the collimator lens 147, and emitted to the sample through the V-block prism 101.

The second optical system 105 includes mirrors 151 and 152, a telemeter lens 153, a beam splitter 154, and the like. The second optical system 105 is fixed to a circular disc 107 mounted to a rotation shaft 161 of a motor 106. Specifically, the mirrors 151 and 152 and the telemeter lens 153 are arranged parallel to the rotation shaft 161 at an eccentric position relative to the rotation shaft 161, and the mirror 152 and the beam splitter 154 are fixed to the circular disc 107 so as to be arranged vertically in a row relative to the rotation shaft 161.

Measurement light passing through the beam splitter 154 is incident on the detector 102 fixed to the circular disc 107. On the other hand, the measurement light reflected on the beam splitter 154 is reflected on a mirror 108, and then, passes through a lens 109 to be guided toward an eyepiece unit (not illustrated) where the state of the measurement light can visually be recognized. The beam splitter 154 and the mirror 108 are provided on the rotation shaft 161. When the position of the V-block prism 101 is adjusted, an auto collimation prism 110 can be interposed on the optical path between the beam splitter 154 and the mirror 108.

With the above configuration, measurement light from the V-block prism 101 can be received at different angles with the rotation of the motor 106, and can be guided to the detector 102. The measurement light from the V-block prism 101 at each rotation angle is detected by the detector 102 by rotating the motor 106. With this, the rotation angle at which the detection intensity becomes the highest can be specified, and the refractive index of the sample can be measured based on this rotation angle and the refractive index of the V-block prism 101.

PRIOR ART DOCUMENTS

Patent Documents

Patent Document 1: JP 2011-99795 A

SUMMARY OF THE INVENTION

Problems to be Solved by the Invention

In the above conventional V-block refractometer, the detector 102 and the auto collimation prism 110 are disposed between the motor 106 and the circular disc 102, so that the distance between the motor 106 and the circular disc 102 has to be increased. Therefore, the conventional refractometer has the problem of being difficult to be downsized, and also has the problem such that, the more the distance is increased, the more the load applied to the motor 106 increases to deteriorate measurement accuracy. When another detector is additionally provided to increase the wavelength range to be measured, the weight is increased to further deteriorate the measurement accuracy.

In the configuration in which measurement light is not visually recognized at the eyepiece unit, but is captured by a camera and the captured image is displayed on a display unit for confirmation, the camera is sometimes mounted on the circular disc 107. Such configuration entails the problem of further deteriorating the measurement accuracy due to the increase in weight, and also entails the problem of requiring consideration for routing cables connected to the camera.

The above conventional V-block refractometer is configured such that measurement light from the light source 133 is reflected horizontally on the mirror 132 and guided to the first optical system 104. Therefore, the measurement light cannot satisfactorily be guided to the first optical system 104 from the mirror 132 depending on the positional relation between the light source 133 and the mirror 132. Specifically, when the reflection angle of the measurement light on the mirror 132 is too large, vignetting with the mirror 132 occurs, and therefore, the light source is difficult to be disposed at the side opposite to the first optical system 104 across the mirror 132. Thus, the problem of the limitation in the arrangement position of the light source 133 occurs.

The present invention is accomplished in view of the above circumstances, and aims to provide a V-block refractometer that can enhance measurement accuracy. The present invention also aims to provide a V-block refractometer that can be made more compact. The present invention also aims to provide a V-block refractometer that can satisfactorily guide measurement light.

Means for Solving the Problems

The refractometer according to the present invention is a V-block refractometer that measures a refractive index of a sample by irradiating the sample with measurement light through a V-block prism, the refractometer comprising: a collimator lens that allows measurement light to be incident on the V-block prism after converting the measurement light into parallel light; a telemeter lens that converges the measurement light passing through the V-block prism; a detector that detects the measurement light from the telemeter lens; a collimator lens holding member that is provided to be rotatable about a predetermined first rotation shaft for holding the collimator lens at an eccentric position relative to the first rotation shaft; and a motor that changes an incident angle of the measurement light incident on the V-block prism from the collimator lens by rotating the collimator lens holding member about the first rotation shaft.

With this configuration, the incident angle of the measurement light incident on the V-block prism from the collimator lens is changed with the rotation of the motor, and the measurement light with each incident angle from the V-block prism is detected by the detector. With this, the incident angle at which the detection intensity becomes the highest can be specified, and the refractive index of the sample can be measured based on this incident angle and the refractive index of the V-block prism. This configuration eliminates the need to provide the detector near the motor as in the conventional art, whereby deterioration in measurement accuracy caused by an increase in load to the motor can be prevented, and the measurement accuracy can be enhanced.

A simple arrangement is only required for the optical system at the downstream side of the V-block prism. Accordingly, the number of the components of the optical system can be reduced, and the degree of freedom of arranging each component can be increased. With this, the structure can be simplified to allow the refractometer to be more compact.

The refractometer may further comprise a first collimator-lens-side mirror that is provided on an axis of the first rotation shaft, and rotates together with the collimator lens holding member about the first rotation shaft to reflect measurement light; and a second collimator-lens-side mirror that is provided at an eccentric position relative to the first rotation shaft, and rotates together with the collimator lens holding member about the first rotation shaft to guide the measurement light reflected on the first collimator-lens-side mirror toward the V-block prism. In this case, it is preferable that measurement light is incident on the first collimator-lens-side mirror along the first rotation shaft.

This configuration can allow measurement light to be incident on the first collimator-lens-side mirror along the first rotation shaft serving as a rotation center of the collimator lens holding member, and can guide the measurement light toward the V-block prism through the first collimator-lens-side mirror and the second collimator-lens-side mirror. With the configuration in which measurement light is incident along the rotation center of the collimator lens holding member as described above, the structure can be more simplified, and the refractometer can be made more compact.

The refractometer may further comprise plurality of light sources, each being capable of emitting measurement light having a different wavelength; a first light-source-side mirror that is provided on an axis of a predetermined second rotation shaft, the first light-source-side mirror receiving the measurement light from the light source according to its rotation position and reflecting the measurement light incident from the light source along the second rotation shaft due to the rotation about the second rotation shaft; and a second light-source-side mirror that guides the measurement light reflected on the first light-source-side mirror toward the collimator lens.

With this configuration, the mirror can be mounted in a double stage structure such that measurement light from the light source is reflected on the first light-source-side mirror, and further reflected on the second light-source-side mirror to be guided toward the collimator lens. The first light-source-side mirror mounted on the axis of the second rotation shaft rotates about the second rotation shaft, and reflects measurement light incident from the light source along the second rotation shaft. With this, measurement light from all light sources can satisfactorily be reflected from the first light-source-side mirror to the second light-source-side mirror, and satisfactorily be guided toward the collimator lens from the second light-source-side mirror, regardless of the rotation position of the first light-source-side mirror.

The refractometer may further comprise a shielding member that covers an exterior of the first light-source-side mirror and is rotatable about the second rotation shaft along with the first light-source-side mirror. In this case, it is preferable that the shielding member has formed thereon an aperture through which only measurement light from one of the light sources according to the rotation position of the first light-source-side mirror is incident.

With this configuration, only measurement light from one light source can be incident on the first light-source-side mirror, and guided toward the collimator lens. Accordingly, this configuration can prevent stray light from other light sources from being incident on the first light-source-side mirror to be guided toward the collimator lens. Consequently, the stray light does not adversely affect the measurement result, whereby the measurement accuracy can be enhanced.

The refractometer according to the present invention is a V-block refractometer that measures a refractive index of a sample by irradiating the sample with measurement light through a V-block prism, the refractometer including: a light source unit having a plurality of light sources, each being capable of emitting measurement light with different wavelengths; a collimator lens that allows measurement light to be incident on the V-block prism after converting the measurement light into parallel light; a telemeter lens that converges the measurement light passing through the V-block prism; and a detector that detects the measurement light from the telemeter lens; wherein the light source unit is provided with a first light-source-side mirror that is mounted on an axis of a predetermined rotation shaft, the first light-source-side mirror receiving the measurement light from the light source according to its rotation position and reflects the measurement light incident from the light source along the rotation shaft due to the rotation about the rotation shaft; and a second light-source-side mirror that guides the measurement light reflected on the first light-source-side mirror toward the collimator lens.

Effects of the Invention

According to the present invention, deterioration in measurement accuracy caused by an increase in load to the motor can be prevented, whereby the measurement accuracy can be enhanced. Further, the structure of the optical system at the downstream side of the V-block prism can be simplified to make the refractometer more compact. In addition, when the mirror is mounted in a double stage structure such that measurement light from the light source is reflected on the first light-source-side mirror and further reflected on the second light-source-side mirror to be guided toward the collimator lens, measurement light from all light sources can satisfactorily be reflected from the first light-source-side mirror to the second light-source-side mirror, and satisfactorily be guided toward the collimator lens from the second light-source-side mirror, regardless of the rotation position of the first light-source-side mirror.

MODE FOR CARRYING OUT THE INVENTION

Figure 1:
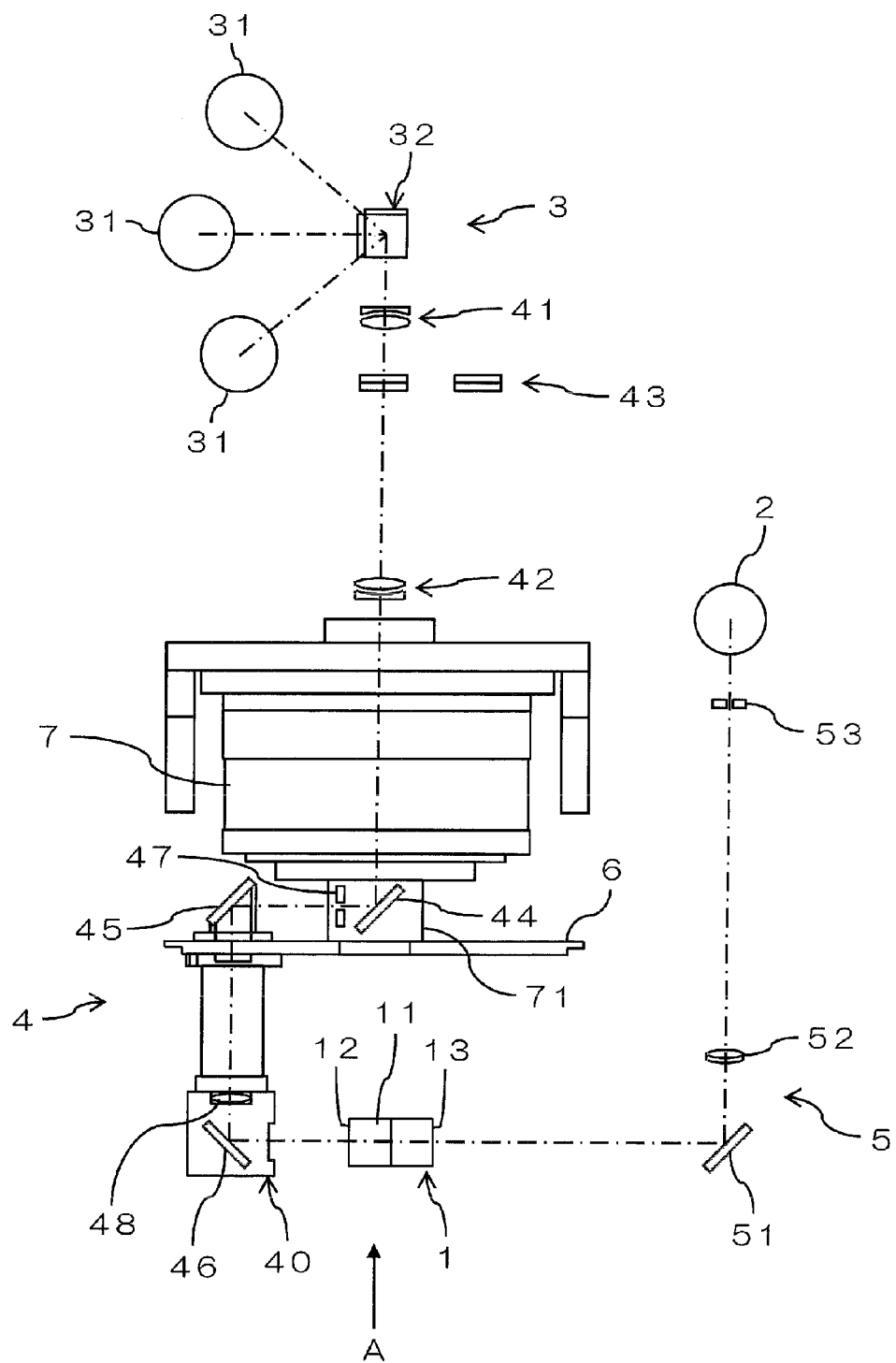
FIG. 1 is a schematic plan view illustrating an example of a configuration of a V-block refractometer according to one embodiment of the present invention.
Figure 2:
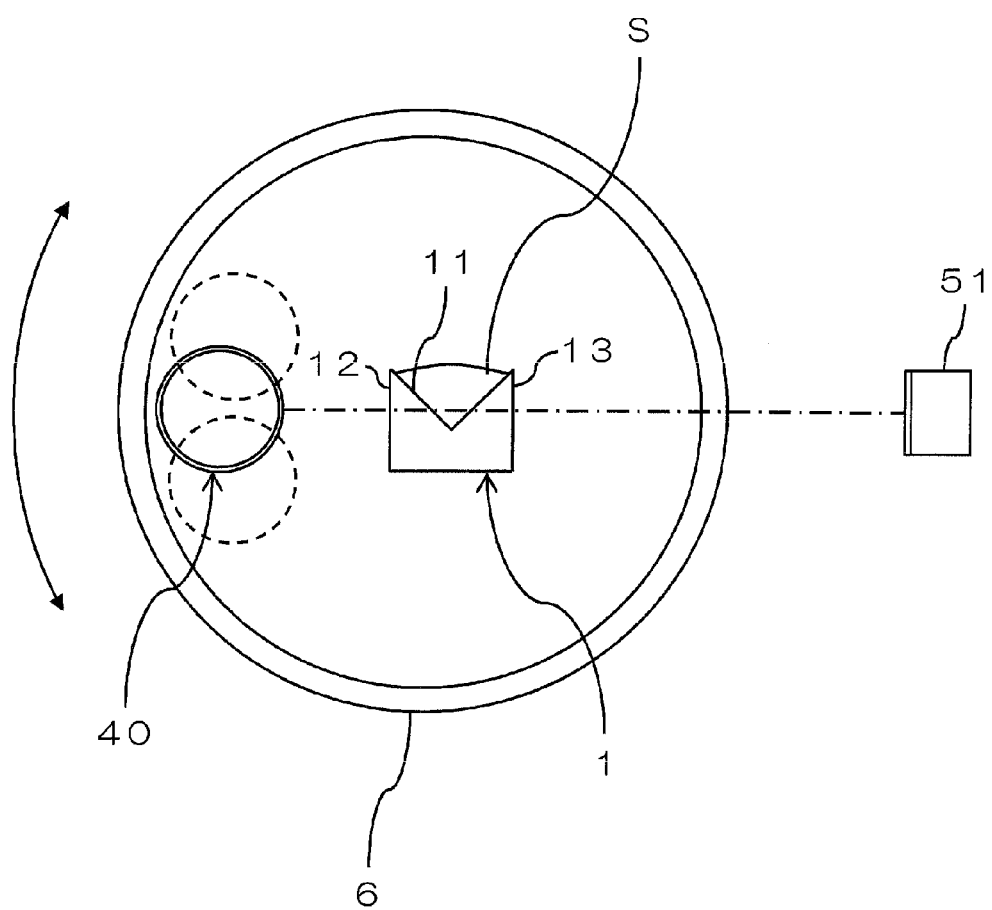
FIG. 2 is a sectional view of the refractometer illustrated in FIG. 1 viewed from an arrow A.

FIG. 1 is a schematic plan view illustrating an example of a configuration of a V-block refractometer according to one embodiment of the present invention. FIG. 2 is a sectional view of the refractometer illustrated in FIG. 1 viewed from an arrow A. This refractometer is a V-block refractometer that measures a refractive index of a sample S by irradiating the sample S with measurement light through a V-block prism 1.

Examples of the sample S include glass, plastic, and liquid. The sample S is placed in a V-shaped groove 11 formed on the V-block prism 1, and the refractive index of the sample S can be measured by detecting measurement light passing through the sample S with a detector 2.

The refractometer includes, in addition to the above V-block prism 1 and the detector 2, a light source unit 3 that emits measurement light, a first optical system 4 that guides the measurement light from the light source unit 3 to the V-block prism 1, and a second optical system 5 that guides the measurement light passing through the V-block prism 1 to the detector 2.

The light source unit 3 includes a plurality of light sources 31. For example, a helium lamp, a hydrogen lamp, or a mercury lamp is used for the light sources 31, and measurement lights, each having a different wavelength such as helium d line, hydrogen C line, hydrogen F line, mercury e line, mercury g line, and mercury h line, can be emitted from the light source unit 3. The measurement light from the light sources 31 is reflected on a plurality of mirrors 32, and emitted in the horizontal direction from the light source unit 3. Notably, the light sources 31 are not limited to the above types.

The first optical system 4 includes lenses 41 and 42, an interference filter 43, mirrors 44, 45, and 46, a slit 47, and a collimator lens 48. The lenses 41 and 42 and the mirror 44 are arranged in a row along the emission direction of the measurement light from the light source unit 3, and any one of a plurality of interference filters 43 can selectively be interposed on an optical path of the measurement light. The plurality of interference filters 43 is selected according to the type of the light sources 31. Only the measurement light (monochromatic light) having a specific wavelength corresponding to the selected interference filter 43 passes through the interference filter 43 and is guided toward the mirror 44.

The mirror 44 is disposed such that the reflection plane tilts at 45 degrees relative to the incidence direction of the measurement light. The measurement light reflected on the mirror 44 changes its advancing direction by 90 degrees, passes through the slit 47, and then, is guided to the mirror 45. The mirror 45 is disposed such that its reflection plane is parallel to the reflection plane of the mirror 44. The measurement light reflected on the mirror 45 changes its advancing direction by 90 degrees, and is guided to the collimator lens 48 along the direction parallel to the emission direction of the measurement light from the light source unit 3.

The collimator lens 48 converts the measurement light into parallel light, and guides the resultant light to the mirror 46. The measurement light, which changes its advancing direction by 90 degrees by the mirror 46, is incident on the V-block prism 1. The mirrors 45 and 46 and the collimator lens 48 are disposed in a row along the direction parallel to the emission direction of the measurement light from the light source unit 3, and integrally held on a circular disc 6 as a collimator unit 40.

The circular disc 6 is a collimator lens holding member for holding the collimator lens 48. The center of the circular disc 6 is fixed to a rotation shaft 71 of a motor 7, whereby the circular disc 6 is rotatable about the rotation shaft 71. The collimator unit 40 is provided to protrude from the circular disc 6 along the direction parallel to the rotation shaft 71 at the eccentric position relative to the rotation shaft 71.

With this, when the circular disc 6 is rotated about the rotation shaft 71 with the rotation of the motor 7, the position of the collimator unit 40 to the V-block prism 1 can be changed (scanned) as indicated by a broken line in FIG. 2, whereby the incident angle of the measurement light incident on the V-block prism 1 can be changed. The motor 7 is a servo motor with an encoder, for example, and can accurately measure the incident angle of the measurement light incident on the V-block prism 1 based on the rotation angle of the motor 7.

Measurement light incident on one end face 12 of the V-block prism 1 passes through the sample S placed in the V-shaped groove 11, passes through the V-block prism 1 again, and is emitted from the other end face 13 at an angle corresponding to the difference in refractive index between the V-block prism 1 and the sample S. In this case, the measurement light is emitted at different angle according to the incident angle to the V-block prism 1, resulting in that a quantity of the measurement light guided to the second optical system 5 is changed according to the incident angle.

The second optical system 5 includes a mirror 51, a telemeter lens 52, and a slit 53. The mirror 51 is disposed on a straight line relative to the mirror 46 and the V-block prism 1, and also disposed such that its reflection plane tilts at 45 degrees relative to the incidence direction of the measurement light. With this, the measurement light reflected on the mirror 51 changes its advancing direction by 90 degrees, and is guided to the telemeter lens 52. The telemeter lens 52 converges the measurement light from the V-block prism 1 and guides the resultant light to the slit 53. The measurement light passing through the slit 53 is detected by the detector 2.

In the present embodiment, the incident angle of the measurement light incident on the V-block prism 1 from the collimator lens 48 is changed with the rotation of the motor 7, and the measurement light with each incident angle from the V-block prism 1 is detected by the detector 2. With this, the incident angle at which the detection intensity becomes the highest can be specified, and the refractive index of the sample S can be measured based on this incident angle and the refractive index of the V-block prism 1. This configuration eliminates the need to provide the detector 2 near the motor 7 as in the conventional art, whereby the distance between the motor 7 and the circular disc 6 can be decreased. Thus, deterioration in measurement accuracy caused by an increase in load to the motor 7 can be prevented, whereby the measurement accuracy can be enhanced.

A simple arrangement is only required for the second optical system 5 at the downstream side of the V-block prism 1. Accordingly, the number of the components of the second optical system 5 can be reduced, and the degree of freedom of arranging each component can be increased. With this, the structure can be simplified to allow the refractometer to be more compact.

If a beam splitter is mounted on the optical path of the second optical system 5 to guide a part of the measurement light passing through the second optical system 5 to an eyepiece unit (not illustrated), the state of the measurement light can visually be recognized at the eyepiece unit. Alternatively, it can be configured such that a part of the measurement light guided through the beam splitter is captured with a camera such as a CCD (Charge Coupled Device) camera, and the captured image is displayed on a display screen of a display unit (not illustrated). Alternatively, it can be configured such that an auto collimation prism (not illustrated) can be interposed on the optical path of the second optical system 5 upon performing the positional adjustment of the V-block prism 1.

With the configuration in which the component such as the beam splitter, camera, or auto collimation prism is provided to the second optical system 5 as described above, deterioration in measurement accuracy caused by an increase in load to the motor 7 can effectively be prevented, compared to the conventional configuration in which these components are disposed near the motor 7.

In the present embodiment, the mirror 44 (first collimator-lens-side mirror) is mounted on the rotation shaft 71 of the motor 7. The mirror 44 rotates with the circular disc 6 about the rotation shaft 71 and reflects measurement light in the radial direction about the rotation shaft 71. For example, the rotation shaft 71 is formed to be hollow, and the mirror 44 is provided in the rotation shaft 71. With this configuration, the mirror 44 can be provided on the axis of the rotation shaft 71 of the motor 7.

On the other hand, the mirror 45 (second collimator-lens-side mirror) is provided at an eccentric position relative to the rotation shaft 71 of the motor 7. The mirror 45 rotates with the circular disc 6 about the rotation shaft 71 and guides the measurement light reflected on the mirror 44 toward the V-block prism 1. The slit 47 may be formed in the rotation shaft 71 of the motor 7 or at the outside of the rotation shaft 71.

In the present embodiment, measurement light is incident on the mirror 44 along the rotation shaft 71 of the motor 7. According to this, measurement light can be incident on the mirror 44 along the rotation shaft 71 serving as the rotation center of the circular disc 6, and can be guided toward the V-block prism 1 through the mirror 44 and the mirror 45. With the configuration in which measurement light is incident along the rotation center of the circular disc 6 as described above, the structure can be more simplified, and the refractometer can be made more compact.

Figure 3:
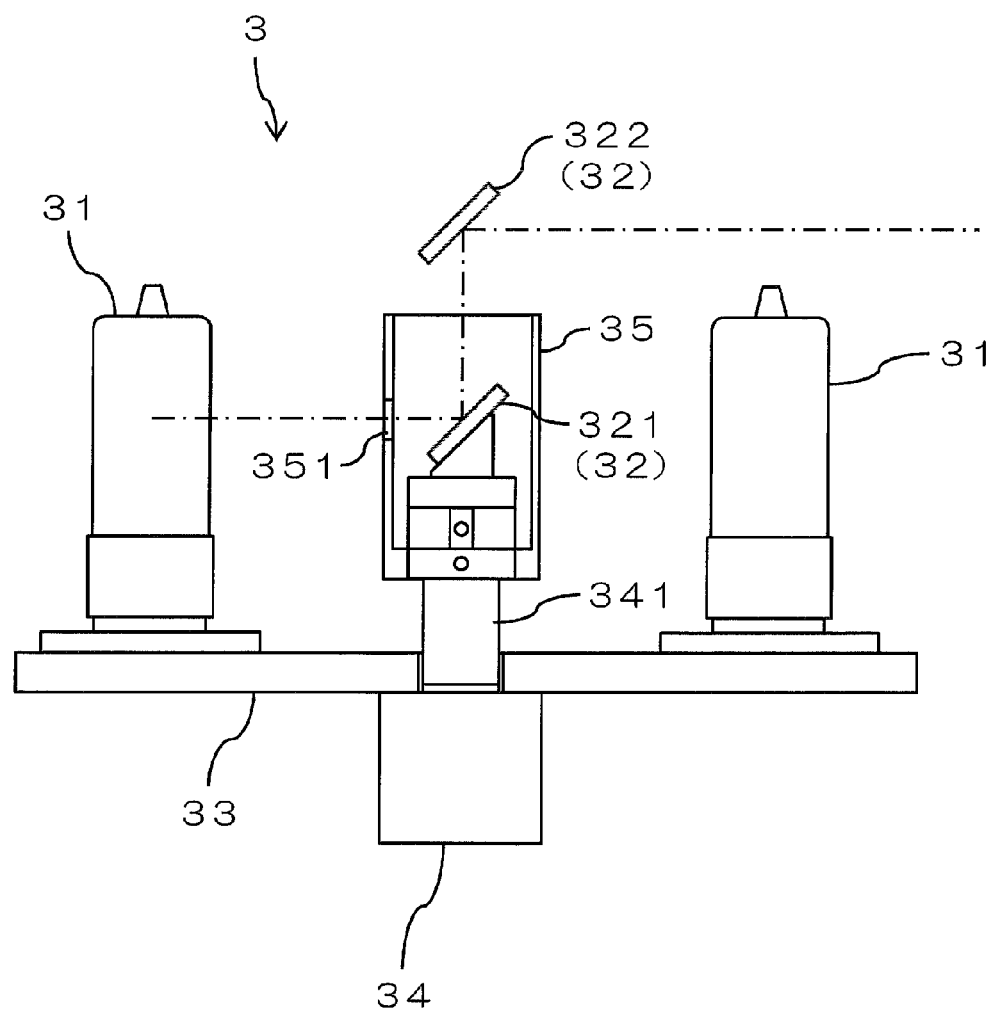
FIG. 3 is a schematic sectional view illustrating the example of the configuration of the light source unit in FIG. 1.

FIG. 3 is a schematic sectional view illustrating the example of the configuration of the light source unit 3 in FIG. 1. In this example, two mirrors 321 and 322 are vertically provided in two stages as the above plurality of mirrors 32. A plurality of light sources 31 is arranged in an arc on a circular holding plate 33. A motor 34 is mounted at the center of the holding plate 33, and a rotation shaft 341 of the motor 34 extends upward through the center of the holding plate 33.

One mirror 321 (first light-source-side mirror) is mounted on an axis of the rotation shaft 341 of the motor 34. The mirror 321 rotates about the rotation shaft 341 with the rotation of the motor 34, thereby being capable of changing the direction of the reflection plane of the mirror 321 by 360 degrees in the circumferential direction. With this, measurement light from the light source 31 according to the rotation position is incident on the reflection plane of the mirror 321.

The reflection plane of the mirror 321 is arranged to tilt at 45 degrees relative to the direction (vertical direction) in which the rotation shaft 341 of the motor 34 extends. Accordingly, the measurement light horizontally incident on the mirror 321 from each light source 31 is reflected to direct upward by changing its advancing direction by 90 degrees. Specifically, the direction of the reflection plane of the mirror 321 is changed with the rotation of the motor 34, and even if the measurement light incident on the reflection plane of the mirror 321 becomes measurement light of another light source 31, the measurement light is always reflected upward along the rotation shaft 341.

The other mirror 322 (second light-source-side mirror) is provided above the mirror 321 on the axis of the rotation shaft 341 of the motor 34. The measurement light reflected upward by the mirror 321 changes its advancing direction by 90 degrees by the mirror 322, and is guided toward the first optical system 4 (toward the collimator lens 48) along the horizontal direction. The mirror 322 is fixed to tilt at 45 degrees relative to the axis of the rotation shaft 341 of the motor 34 so as to always reflect measurement light in a fixed direction.

As described above, in the present embodiment, the mirror 32 can be mounted in a double stage structure such that measurement light from the light source 31 is reflected by the mirror 321, and further reflected by the mirror 322 to be guided toward the collimator lens 48. The mirror 321 provided on the axis of the rotation shaft 341 of the motor 34 rotates about the rotation shaft 341, and reflects measurement light incident from the light source 31 along the rotation shaft 341. With this, measurement light from all light sources 31 can satisfactorily be reflected from the mirror 321 to the mirror 322, and satisfactorily be guided toward the collimator lens 48 from the mirror 322, regardless of the rotation position of the mirror 321.

In the present embodiment, a cylindrical shielding member 35 is mounted to the rotation shaft 341 of the motor 34, and the mirror 321 is mounted in the shielding member 35. Specifically, the exterior of the mirror 321 is covered by the shielding member 35 which can rotate with the mirror 321 about the rotation shaft 341 of the motor 34. An aperture 351 is formed on the wall face of the shielding member 35 at the position opposite to the reflection plane of the mirror 321 in the horizontal direction. With this, only measurement light from one light source 31 according to the rotation position of the mirror 321 can be incident on the mirror 321 from the aperture 351.

As described above, in the present embodiment, only measurement light from one light source 31 can be incident on the mirror 321, and guided toward the collimator lens 48. Accordingly, this configuration can prevent stray light from other light sources 31 from being incident on the mirror 321 to be guided toward the collimator lens 48. Consequently, the stray light does not adversely affect the measurement result, whereby the measurement accuracy can be enhanced.

Figure 4:
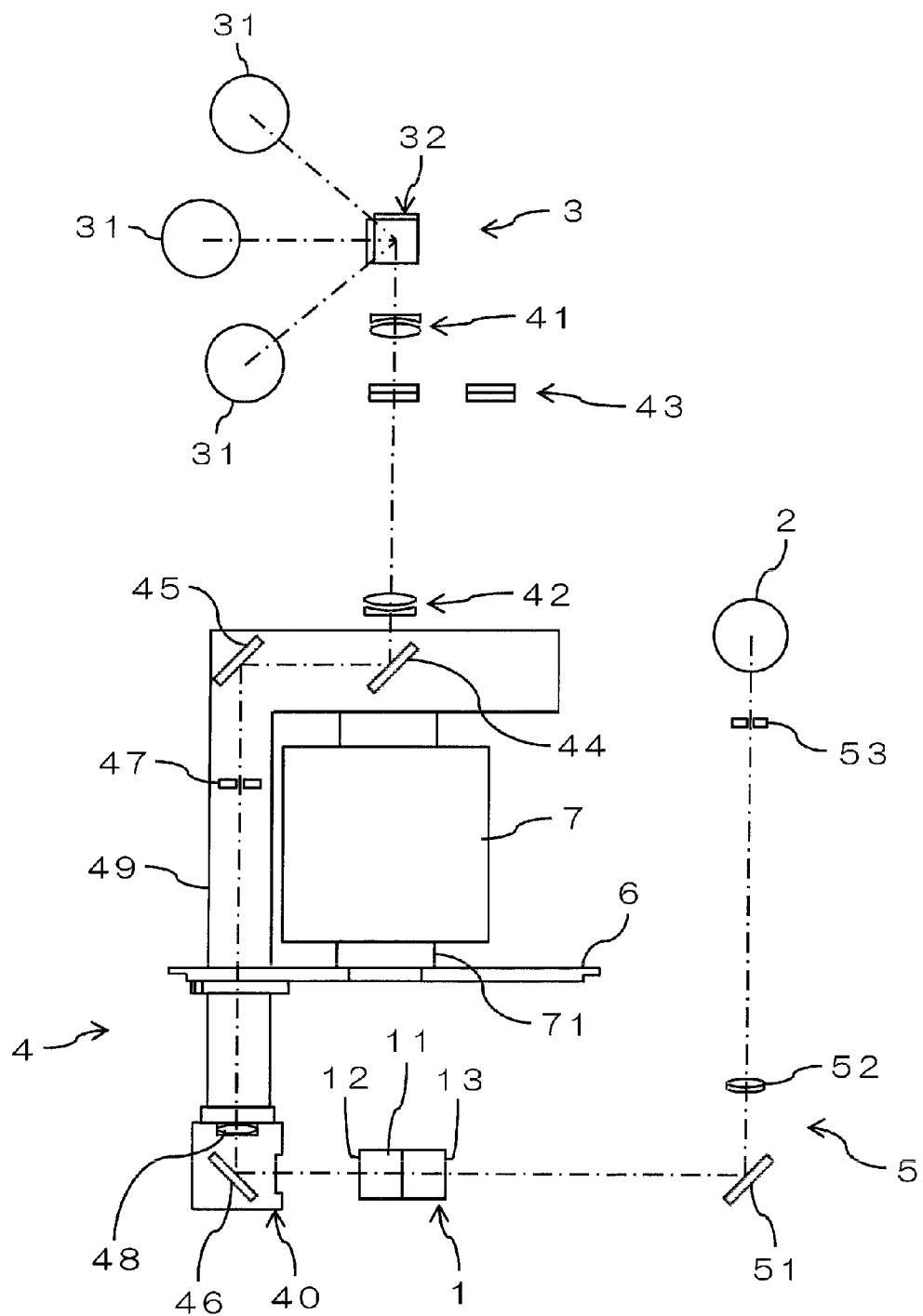
FIG. 4 is a schematic plan view illustrating an example of a configuration of a V-block refractometer according to another embodiment.
Figure 5:
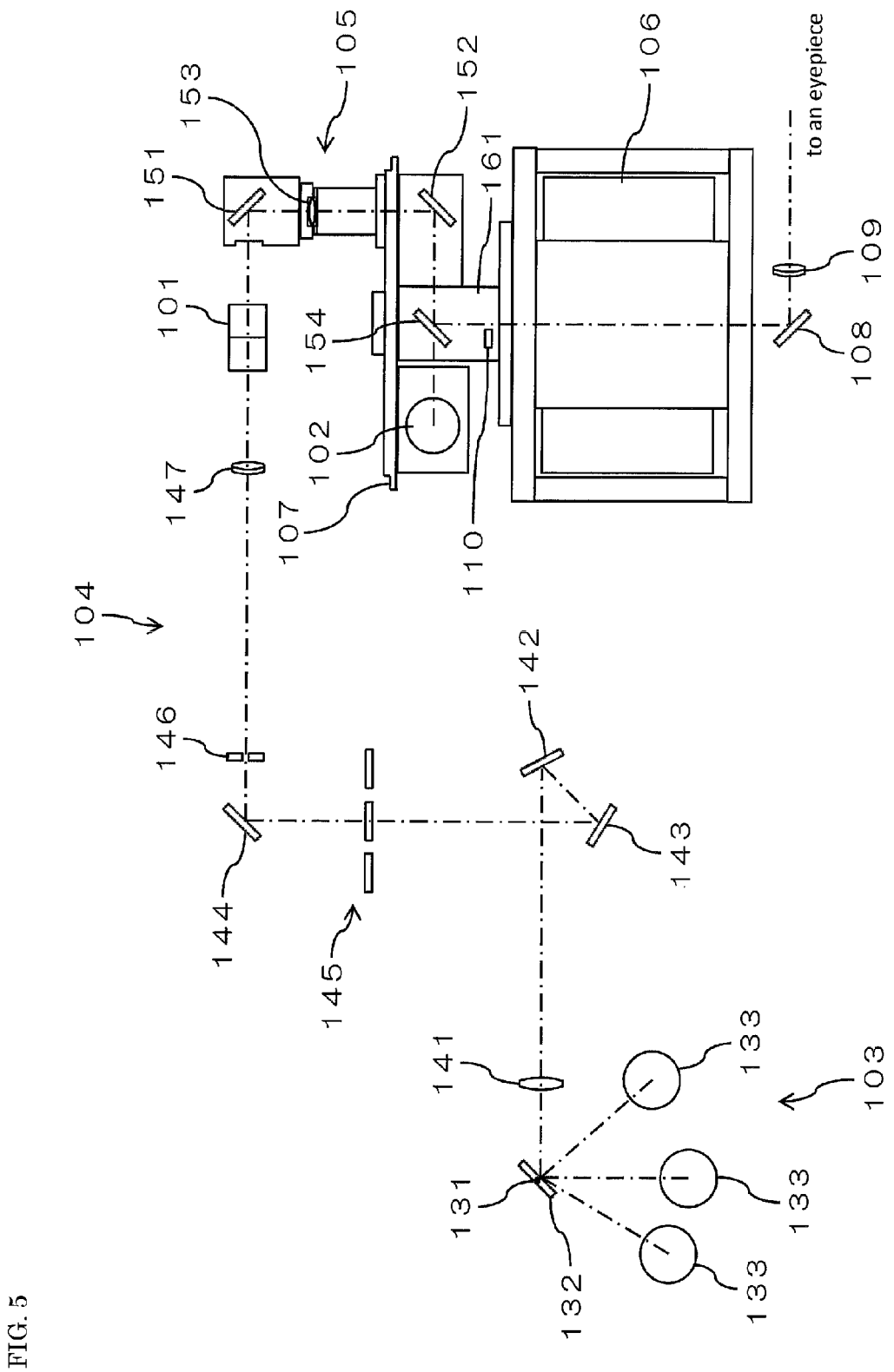
FIG. 5 is a schematic plan view illustrating an example of a configuration of a conventional V-block refractometer.

FIG. 4 is a schematic plan view illustrating an example of a configuration of a V-block refractometer according to another embodiment. In the present embodiment, the arrangement position of the mirrors 44 and 45 and the slit 47 in the first optical system 4 is different from the above embodiment, and the other configurations are similar to the above embodiment. Therefore, the similar configurations are identified by the same reference numerals, and the detailed description will not be repeated.

In the present embodiment, the mirrors 44 and 45 are not provided close to the circular disc 6 with respect to the motor 7, but provided to the opposite side of the circular disc 6, i.e., close to the light source unit 3. Specifically, an L-shaped holding member 49 rotating together with the rotation shaft 71 of the motor 7 is connected to the circular disc 6 along the side of the motor 7 from the light source unit 3 side with respect to the motor 7, and the mirrors 44 and 45 and the slit 47 are provided to this holding member 49.

The mirror 44 is disposed such that the reflection plane tilts at 45 degrees relative to the incidence direction of the measurement light. The measurement light reflected on the mirror 44 changes its advancing direction by 90 degrees, and then, is guided to the mirror 45. The mirror 45 is disposed such that its reflection plane is parallel to the reflection plane of the mirror 44. The measurement light reflected on the mirror 45 changes its advancing direction by 90 degrees, and is guided to the slit 47 in the direction parallel to the emission direction of the measurement light from the light source unit 3. The measurement light passing through the slit 47 is incident on the collimator lens 48.

The mirror 44 (first collimator-lens-side mirror) is mounted on the axis of the rotation shaft 71 of the motor 7. The mirror 44 rotates with the circular disc 6 about the rotation shaft 71 and reflects measurement light in the radial direction about the rotation shaft 71. On the other hand, the mirror 45 (second collimator-lens-side mirror) is provided at an eccentric position relative to the rotation shaft 71 of the motor 7. The mirror 45 rotates with the circular disc 6 about the rotation shaft 71 and guides the measurement light reflected on the mirror 44 toward the V-block prism 1.

In the present embodiment as well, measurement light is incident on the mirror 44 along the rotation shaft 71 of the motor 7 as in the above embodiment. According to this, measurement light can be incident on the mirror 44 along the rotation shaft 71 serving as the rotation center of the circular disc 6, and can be guided toward the V-block prism 1 through the mirror 44 and the mirror 45. With the configuration in which measurement light is incident along the rotation center of the circular disc 6 as described above, the structure can be more simplified, and the refractometer can be made more compact.

Especially in the present embodiment, the mirror 44 is not provided in the rotation shaft 71 of the motor 7 as in the above embodiment. Therefore, it is unnecessary to form the rotation shaft 71 of the motor 7 to be hollow, and the distance between the motor 7 and the circular disc 6 can further be decreased. In addition, the circular disc 6 is connected not only to the rotation shaft 71 but also to the holding member 49, whereby rigidity of the circular disc 6 is increased. Accordingly, deterioration in measurement accuracy caused by an increase in load to the motor 7 can effectively be prevented, whereby the measurement accuracy can further be enhanced.

The above embodiments describe the configuration in which measurement light is guided to the detector 2 from the light source unit 3 along the horizontal direction. However, the configuration is not limited thereto. At least a part of the optical path of the measurement light from the light source unit 3 to the detector 2 may tilt relative to the horizontal direction. In this case, the rotation shaft 71 of the motor 7 is not limited to extend in the horizontal direction. The rotation shaft 71 may extend in the tilting direction relative to the horizontal direction.

The configuration of the optical member provided on the optical path of the measurement light from the light source unit 3 to the detector 2 is not limited to the configuration illustrated in the above embodiments. Another optical member may be provided, and a part of the optical members may be eliminated.

The other configurations may be different from the above embodiments, so long as it is configured such that an incident angle of measurement light incident on the V-block prism 1 from the collimator lens 48 is changed by rotating the circular disc 6 about the rotation shaft 71 using the motor 7. For example, measurement light from the light source unit 3 may not be incident on the mirror 44 along the rotation shaft 71, but may be incident from an eccentric position relative to the rotation shaft 71. The light source unit 3 is not limited to have the double stage structure including two mirrors 321 and 322. The light source unit 3 may be configured to guide measurement light from the light source 31 using one mirror or three or more mirrors.

DESCRIPTION OF REFERENCE SIGNS

1 V-block prism
2 detector
3 light source unit
4 first optical system
5 second optical system
6 circular disc
7 motor
31 light source
32 mirror
33 holding plate
34 motor
35 shielding member
40 collimator unit
41, 42 lens
43 interference filter
44, 45, 46 mirror
47 slit
48 collimator lens
49 holding member
51 mirror
52 telemeter lens
53 slit
71 rotation shaft
321, 322 mirror
341 rotation shaft
351 aperture
S sample

The invention claimed is:

1. A V-block refractometer that measures a refractive index of a sample by irradiating the sample with measurement light through a V-block prism, the refractometer comprising:
    a collimator lens that allows measurement light to be incident on the V-block prism after converting the measurement light into parallel light;
    a telemeter lens that converges the measurement light passing through the V-block prism;
    a detector that detects the measurement light from the telemeter lens;
    a collimator lens holding member that is provided to be rotatable about a predetermined first rotation shaft for holding the collimator lens at an eccentric position relative to the first rotation shaft; and
    a motor that changes an incident angle of the measurement light incident on the V-block prism from the collimator lens by rotating the collimator lens holding member about the first rotation shaft.

2. The V-block refractometer according to claim 1, further comprising:
    a first collimator-lens-side mirror that is provided on an axis of the first rotation shaft, and rotates together with the collimator lens holding member about the first rotation shaft to reflect measurement light; and
    a second collimator-lens-side mirror that is provided at an eccentric position relative to the first rotation shaft, and rotates together with the collimator lens holding member about the first rotation shaft to guide the measurement light reflected on the first collimator-lens-side mirror toward the V-block prism, wherein
    measurement light is incident on the first collimator-lens-side mirror along the first rotation shaft.

3. The V-block refractometer according to claim 1, further comprising:
    plurality of light sources, each being capable of emitting measurement light having a different wavelength;
    a first light-source-side mirror that is provided on an axis of a predetermined second rotation shaft, the first light-source-side mirror receiving the measurement light from the light source according to its rotation position and reflecting the measurement light incident from the light source along the second rotation shaft due to the rotation about the second rotation shaft; and
    a second light-source-side mirror that guides the measurement light reflected on the first light-source-side mirror toward the collimator lens.

4. The V-block refractometer according to claim 3, further comprising:
    a shielding member that covers an exterior of the first light-source-side mirror and is rotatable about the second rotation shaft along with the first light-source-side mirror, wherein
    the shielding member has formed thereon an aperture through which only measurement light from one of the light sources according to the rotation position of the first light-source-side mirror is incident.

* * * * *